United States Patent
Bonnet et al.

(10) Patent No.: US 10,532,966 B2
(45) Date of Patent: Jan. 14, 2020

(54) METHOD FOR PRODUCING FLUORINATED COMPOUNDS

(71) Applicant: Arkema France, Colombes (FR)

(72) Inventors: Philippe Bonnet, Lyons (FR);
Bertrand Collier, Saint-Genis-Laval (FR); Dominique Deur-Bert, Charly (FR); Dominique Garrait, Charly (FR);
Anne Pigamo, Francheville (FR);
Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 15/861,873

(22) Filed: Jan. 4, 2018

(65) Prior Publication Data
US 2018/0141885 A1 May 24, 2018

Related U.S. Application Data

(62) Division of application No. 15/028,798, filed as application No. PCT/FR2014/052593 on Oct. 13, 2014, now Pat. No. 9,938,210.

(30) Foreign Application Priority Data

Oct. 17, 2013 (FR) ..................... 13 60101

(51) Int. Cl.
*C07C 17/00* (2006.01)
*C07C 17/20* (2006.01)
(Continued)

(52) U.S. Cl.
CPC ............... *C07C 17/206* (2013.01); *B01J 7/00* (2013.01); *C07C 17/21* (2013.01); *C07C 17/25* (2013.01)

(58) Field of Classification Search
CPC ....... C07C 17/00; C07C 17/093; C07C 17/20; C07C 17/202; C07C 17/206; C07C 17/21;
(Continued)

(56) References Cited

U.S. PATENT DOCUMENTS 2,744,147 A * 5/1956 Milks ........................ B01J 27/06
502/228
6,034,288 A * 3/2000 Scott ........................ B01D 1/14
570/102

(Continued)

FOREIGN PATENT DOCUMENTS

| CN | 101 074 185 A | 11/2007 |
| WO | WO-2013/088195 A1 | 6/2013 |
| WO | WO-2014/159975 A1 | 10/2014 |

OTHER PUBLICATIONS

"Hydrogen Fluoride, Anhydrous," CAMEO Chemicals—Chemical Datasheet, pp. 1-5.
(Continued)

*Primary Examiner* — Natasha E Young
(74) *Attorney, Agent, or Firm* — NK Patent Law

(57) ABSTRACT

A method for producing a fluorinated compound comprises: the provision of a gaseous flow comprising hydrofluoric acid; the provision of at least one liquid flow of a chlorinated compound and the vapourisation thereof by mixing with the gaseous flow, the resulting mixture being a gaseous mixture; and the catalytic reaction of the chlorinated compound with hydrofluoric acid in a gaseous phase and the collection of a product flow. The invention also relates to a facility for carrying out the method.

8 Claims, 2 Drawing Sheets

(51) Int. Cl.
*C07C 17/21* (2006.01)
*C07C 17/25* (2006.01)
*B01J 7/00* (2006.01)

(58) Field of Classification Search
CPC ......... C07C 17/25; C07C 19/00; C07C 19/08;
C07C 21/00; C07C 21/02; C07C 21/18;
B01J 7/00
See application file for complete search history.

(56) References Cited

U.S. PATENT DOCUMENTS

| | | | |
|---|---|---|---|
| 6,035,288 A | 3/2000 | Scott et al. | |
| 2012/0123172 A1* | 5/2012 | Hibino | B01J 21/04 |
| | | | 570/160 |
| 2014/0275647 A1 | 9/2014 | Merkel et al. | |

OTHER PUBLICATIONS

Thakur, R.K. et al, "Static Mixers in the Process Industries-A Review", Trans IChemE, Aug. 2003, pp. 787-826, vol. 81, Part A.

* cited by examiner

METHOD FOR PRODUCING FLUORINATED COMPOUNDS

CROSS-REFERENCE TO RELATED APPLICATIONS

This application is a Divisional of U.S. patent application Ser. No. 15/028,798, now U.S. Pat. No. 9,938,210, filed Apr. 12, 2016, now allowed; which is a National Stage application of International Application No. PCT/FR2014/052593, now WO/2015/055927, filed Oct. 13, 2014. This application also claims priority under 35 U.S.C. § 119 to French Application No. 1360101 filed Oct. 17, 2013.

FIELD OF THE INVENTION

The present invention relates to a process for producing fluoro compounds, such as hydrofluoroolefins or fluorohydrocarbons, for example, and to an installation adapted to the implementation of this process.

TECHNICAL BACKGROUND

It is known practice to produce hydrofluoroolefins or fluorohydrocarbons by fluorination of hydrochloroolefins or chlorohydrocarbons, especially. This fluorination is generally a catalytic fluorination using hydrofluoric acid as fluorinating agent.

The fluorination reaction must generally be performed at a high temperature (above 300° C.) in the gas phase. Consequently, it is known practice to heat, vaporize and superheat the reagents before the fluorination reaction, using heat exchangers.

However, this preliminary step of heating, vaporization and superheating of the reagents has a tendency to lead to the production of coke in the heat exchangers.

There is thus a need to develop a process for producing fluoro compounds that limits or avoids the problem of coking of the installation.

SUMMARY OF THE INVENTION

The invention relates firstly to a process for producing a fluoro compound, involving:
  supplying a gas stream comprising hydrofluoric acid;
  supplying at least one liquid stream of chloro compound and vaporizing said compound by mixing with said gas stream, the resulting mixture being a gaseous mixture;
  catalytically reacting the chloro compound with the hydrofluoric acid in the gas phase and collecting a product stream.
  According to one embodiment:
  the chloro compound is a chlorocarbon, a chlorohydrocarbon, a chlorofluorocarbon, a hydrochlorofluorocarbon, a chloroolefin, a hydrochloroolefin, a chlorofluoroolefin or a hydrochlorofluoroolefin; and the fluoro compound is a fluorocarbon, a fluorohydrocarbon, a chlorofluorocarbon, a hydrochlorofluorocarbon, a fluoroolefin, a hydrofluoroolefin, a chlorofluoroolefin or a hydrochlorofluoroolefin; and
  preferably, the chloro compound is chosen from 1,1,2-trichloroethane, 1,1,1,2,3-pentachloropropane, 1,1,1,3,3-pentachloropropane, 1,1,2,2,3-pentachloropropane, 2,3-dichloro-1,1,1-trifluoropropane, perchloroethylene, 1,2-dichloroethylene, 1,1,2,3-tetrachloropropene, 2,3,3,3-tetrachloropropene, 1,1,3,3-tetrachloropropene, 1,3,3,3-tetrachloropropene, 2-chloro-3,3,3-trifluoropropene and 1-chloro-3,3,3-trifluoropropene, and mixtures thereof;
  preferably, the fluoro compound is chosen from pentafluoroethane, 1-chloro-2,2-difluoroethane, 1,3,3,3-tetrafluoropropene, 2,3,3,3-tetrafluoropropene, 2-chloro-3,3,3-trifluoropropene and 1-chloro-3,3,3-trifluoropropene, and mixtures thereof;
  more particularly preferably, the chloro compound is perchloroethylene and the fluoro compound is pentafluoroethane, or the chloro compound is 1,1,1,2,3-pentachloropropane and the fluoro compound is 2,3,3,3-tetrafluoropropene.

According to another embodiment, the chloro compound is 1,1,3,3-tetrachloropropene and the fluoro compound is 1-chloro-3,3,3-trifluoropropene; or the chloro compound is 1-chloro-3,3,3-trifluoropropene and the fluoro compound is 1,3,3,3-tetrafluoropropene; or the chloro compound is 1,1,2-trichloroethane and the fluoro compound is 1-chloro-2,2-difluoroethane.

According to one embodiment, the mixing of the liquid stream of chloro compound with the gas stream comprising hydrofluoric acid is performed in a static mixer.

According to one embodiment, the process comprises one or more steps of separating the product stream, making it possible to collect, on the one hand, a stream of fluoro compound and, on the other hand, a recycling stream.

According to one embodiment, the recycling stream provides the gas stream comprising hydrofluoric acid, optionally after supplying hydrofluoric acid.

According to one embodiment, the process comprises a step of catalytic fluorination of the recycling stream, where appropriate with a supply of hydrofluoric acid, the gas stream comprising hydrofluoric acid being collected on conclusion of this fluorination step.

According to one embodiment, the process comprises a step of heating the liquid stream of chloro compound to a temperature below its vaporization temperature.

According to one embodiment, the process comprises, after the step of mixing the liquid stream of chloro compound with the gas stream comprising hydrofluoric acid, and before the step of catalytic reaction of the chloro compound with the hydrofluoric acid:
  a step of heating the mixture; or
  a step of cooling the mixture.

The invention also relates to an installation for producing a fluoro compound, comprising:
  a pipe for supplying a liquid stream of chloro compound;
  a pipe for supplying a gas stream comprising hydrofluoric acid;
  a mixing and vaporizing unit fed by the pipe for supplying the liquid stream of chloro compound and the pipe for supplying the gas stream comprising hydrofluoric acid;
  a pipe for collecting a gas mixture at the outlet of the mixing and vaporizing unit;
  a catalytic fluorination reactor fed by the pipe for collecting the gas mixture; and
  a pipe for collecting the product stream at the outlet of the catalytic fluorination reactor.
  According to one embodiment:
  the chloro compound is a chlorocarbon, a chlorohydrocarbon, a chlorofluorocarbon, a hydrochlorofluorocarbon, a chloroolefin, a hydrochloroolefin or a hydrochlorofluoroolefin; and the fluoro compound is a fluorocarbon, a fluorohydrocarbon, a chlorofluorocarbon, a hydrochlorofluorocarbon, a fluoroolefin, a hydrofluoroolefin or a hydrochlorofluoroolefin; and preferably, the chloro compound is chosen from 1,1,2-trichloroethane, 1,1,1,2,3-pentachloropropane, 1,1,1,3,3-pentachloropropane, 1,1,2,2,3-pentachloropropane, 2,3-dichloro-1,1,1-trifluoropropane, perchloroethylene, 1,2-dichloroethylene, 1,1,2,3-tetrachloropropene, 2,3,3,3-tetrachloropropene, 1,1,3,3-tetrachloropropene, 1,3,3,3-tetrachloropropene, 2-chloro-3,3,3-trifluoropropene and 1-chloro-3,3,3-trifluoropropene, and mixtures thereof;

preferably, the fluoro compound is chosen from pentafluoroethane, 1-chloro-2,2-difluoroethane, 1,3,3,3-tetrafluoropropene, 2,3,3,3-tetrafluoropropene, 2-chloro-3,3,3-trifluoropropene and 1-chloro-3,3,3-trifluoropropene, and mixtures thereof;

more particularly preferably, the chloro compound is perchloroethylene and the fluoro compound is pentafluoroethane, or the chloro compound is 1,1,1,2,3-pentachloropropane and the fluoro compound is 2,3,3,3-tetrafluoropropene.

According to another embodiment, the chloro compound is 1,1,3,3-tetrachloropropene and the fluoro compound is 1-chloro-3,3,3-trifluoropropene; or the chloro compound is 1-chloro-3,3,3-trifluoropropene and the fluoro compound is 1,3,3,3-tetrafluoropropene; or the chloro compound is 1,1,2-trichloroethane and the fluoro compound is 1-chloro-2,2-difluoroethane.

According to one embodiment, the mixing and vaporizing unit is a static mixer.

According to one embodiment, the installation comprises:
at least one separating unit fed by the product stream collection pipe; and
a fluoro compound collection pipe and a recycling stream collection pipe at the outlet of the separating unit(s).

According to one embodiment, the recycling stream collection pipe and optionally a hydrofluoric acid supply pipe feed the pipe for supplying the gas stream comprising hydrofluoric acid.

According to one embodiment, the installation comprises a catalytic fluorination reactor fed at least partly by the recycling stream collection pipe, where appropriate with a supply of hydrofluoric acid, the pipe for supplying the gas stream comprising hydrofluoric acid being derived from the catalytic fluorination reactor.

According to one embodiment, the installation comprises heating means on the pipe for supplying the liquid stream of chloro compound.

According to one embodiment, the installation comprises heating means or cooling means on the gas mixture collection pipe.

The present invention makes it possible to overcome the drawbacks of the prior art. It more particularly provides a process for producing fluoro compounds which limits or avoids the problem of coking of the installation.

This is accomplished by vaporizing the main reagent (chloro compound intended to be fluorinated) by mixing it with a hot gas stream which contains hydrofluoric acid.

Vaporizing and superheating of the main reagent in a heat exchanger is thus avoided, this heat exchanger having a very high contact surface and also hotspots, which are two factors that lead to substantial coking (the hot metal having a tendency to catalyze coking).

Moreover, as a result of this mixing step, the partial pressure of the chloro compound during its vaporization is relatively moderate, and thus the vaporization temperature is also relatively moderate, and in any case below the vaporization temperature in the situation in which the chloro compound is vaporized independently. This makes it possible especially to limit the risks of degradation of the chloro compound.

Preferably, the gas stream comprising hydrofluoric acid is at a temperature from 100 to 400° C., more particularly from 130 to 380° C. and advantageously from 250 to 380° C. at the time of its mixing with the liquid stream of chloro compound.

In general, the temperature of the gas stream comprising hydrofluoric acid, at the time of its mixing with the liquid stream of chloro compound, is chosen:
less than or equal to the temperature of the catalytic reaction;
greater than or equal to the vaporization temperature of the gas stream comprising hydrofluoric acid, which depends on the pressure and the composition of this stream (especially the HF content).

For example, in the context of producing HFC-125 (as described in greater detail hereinbelow), the temperature of the gas stream comprising hydrofluoric acid may be about 165° C. In the context of producing HFO-1234yf (as described in greater detail hereinbelow), the temperature of the gas stream comprising hydrofluoric acid may be from about 320 to 380° C.

DESCRIPTION OF EMBODIMENTS OF THE INVENTION

Figure 1:
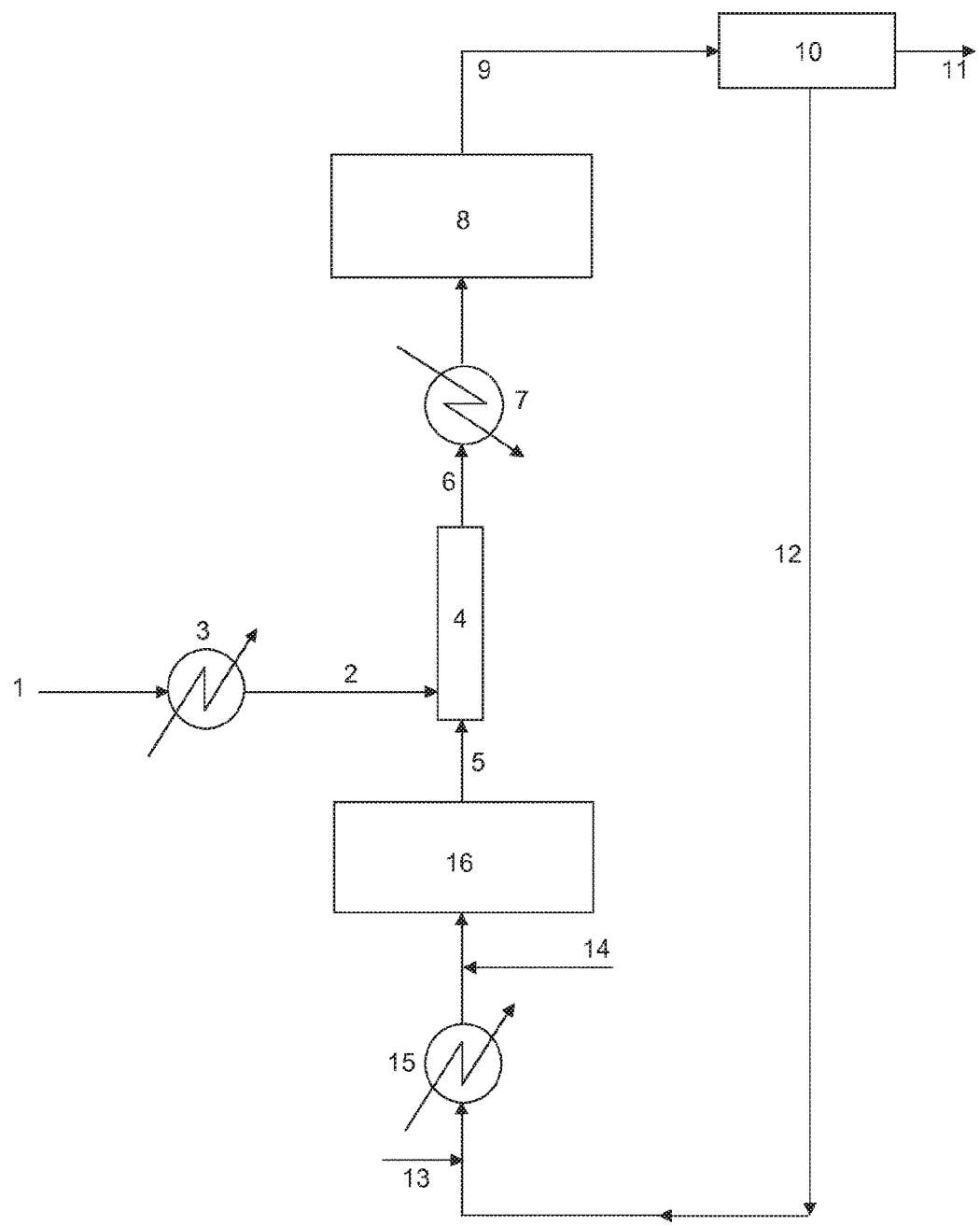
FIG. 1 schematically represents one embodiment of the installation according to the invention.

The invention is now described in greater detail and in a nonlimiting manner in the description that follows.

The invention relates to the fluorination of a chloro compound with hydrofluoric acid, to form a fluoro compound.

The term "chloro compound" means an organic compound comprising one or more chlorine atoms, and the term "fluoro compound" means an organic compound comprising one or more fluorine atoms.

It is understood that the chloro compound may comprise one or more fluorine atoms, and that the fluoro compound may comprise one or more chlorine atoms. In general, the number of chlorine atoms in the fluoro compound is less than the number of chlorine atoms in the chloro compound; and the number of fluorine atoms in the fluoro compound is greater than the number of fluorine atoms in the chloro compound.

The chloro compound may be an alkane or an alkene optionally bearing substituents chosen from F, Cl, I and Br (preferably from F and Cl), and comprising at least one Cl substituent. The fluoro compound may be an alkane or an alkene optionally bearing substituents chosen from F, Cl, I and Br (preferably from F and Cl), and comprising at least one F substituent.

The chloro compound may especially be an alkane with one or more chlorine substituents (chlorohydrocarbon or chlorocarbon) or an alkane with one or more chlorine and fluorine substituents (hydrochlorofluorocarbon or chlorofluorocarbon) or an alkene with one or more chlorine substituents (chloroolefin or hydrochloroolefin) or an alkene with one or more chlorine and fluorine substituents (hydrochlorofluoroolefin or chlorofluoroolefin).

The fluoro compound may especially be an alkane with one or more fluorine substituents (fluorocarbon or hydrofluorocarbon) or an alkane with one or more chlorine and fluorine substituents (hydrochlorofluorocarbon or chlorofluorocarbon) or an alkene with one or more fluorine substituents (fluoroolefin or hydrofluoroolefin) or an alkene with one or more chlorine and fluorine substituents (hydrochlorofluoroolefin or chlorofluoroolefin).

The chloro compound and the fluoro compound may be linear or branched, preferably linear.

According to one embodiment, the chloro compound and the fluoro compound comprise only one carbon atom.

According to one embodiment, the chloro compound and the fluoro compound comprise two carbon atoms.

According to one embodiment, the chloro compound and the fluoro compound comprise three carbon atoms.

According to one embodiment, the chloro compound and the fluoro compound comprise four carbon atoms.

According to one embodiment, the chloro compound and the fluoro compound comprise five carbon atoms.

The invention is especially to be applied for the following fluorination reactions:

fluorination of perchloroethylene (PER) to pentafluoroethane (HFC-125);
fluorination of 1,1,1,2,3-pentachloropropane (HCC-240db) to 2-chloro-3,3,3-trifluoropropene (HCFO-1233xf);
fluorination of 1,1,1,2,3-pentachloropropane (HCC-240db) to 2,3,3,3-tetrafluoropropene (HFO-1234yf);
fluorination of 1,1,1,3,3-pentachloropropane (HCC-240fa) to 1,3,3,3-tetrafluoropropene (HFO-1234ze);
fluorination of 1,1,1,3,3-pentachloropropane (HCC-240fa) to 1-chloro-3,3,3-trifluoropropene (HFO-1233zd);
fluorination of 2-chloro-3,3,3-trifluoropropene (HCFO-1233xf) to 2,3,3,3-tetrafluoropropene (HFO-1234yf);
fluorination of 1,1,2,2,3-pentachloropropane (HCC-240aa) to 2,3,3,3-tetrafluoropropene (HFO-1234yf);
fluorination of 1,1,2,2,3-pentachloropropane (HCC-240aa) to 2-chloro-3,3,3-trifluoropropene (HFO-1233xf);
fluorination of 2,3-dichloro-1,1,1-trifluoropropane (HCFC-243db) to 2,3,3,3-tetrafluoropropene (HFO-1234yf);
fluorination of 2,3-dichloro-1,1,1-trifluoropropane (HCFC-243db) to 1-chloro-3,3,3-trifluoropropene (HFO-1233zd);
fluorination of 2,3-dichloro-1,1,1-trifluoropropane (HCFC-243db) to 1,3,3,3-tetrafluoropropene (HFO-1234ze);
fluorination of 2,3-dichloro-1,1,1-trifluoropropane (HCFC-243db) to 2-chloro-3,3,3-trifluoropropene (HFO-1233xf);
fluorination of 1,1,2,3-tetrachloropropene (HCO-1230xa) to 2,3,3,3-tetrafluoropropene (HFO-1234yf);
fluorination of 1,1,2,3-tetrachloropropene (HCO-1230xa) to 2-chloro-3,3,3-trifluoropropene (HFO-1233xf);
fluorination of 2,3,3,3-tetrachloropropene (HCO-1230xf) to 2,3,3,3-tetrafluoropropene (HFO-1234yf);
fluorination of 2,3,3,3-tetrachloropropene (HCO-1230xf) to 2-chloro-3,3,3-trifluoropropene (HCFO-1233xf);
fluorination of 1,1,3,3-tetrachloropropene (HCO-1230za) to 1-chloro-3,3,3-trifluoropropene (HFO-1233zd);
fluorination of 1,1,3,3-tetrachloropropene (HCO-1230za) to 1,3,3,3-tetrafluoropropene (HFO-1234ze);
fluorination of 1,3,3,3-tetrachloropropene (HCO-1230zd) to 1-chloro-3,3,3-trifluoropropene (HFO-1233zd);
fluorination of 1,3,3,3-tetrachloropropene (HCO-1230zd) to 1,3,3,3-tetrafluoropropene (HFO-1234ze);
fluorination of 1-chloro-3,3,3-trifluoropropene (HFO-1233zd) to 1,3,3,3-tetrafluoropropene (HFO-1234ze);
fluorination of 1,1,2-trichloroethane to 1-chloro-2,2-difluoroethane (HCFC-142);
fluorination of 1,2-dichloroethylene to 1-chloro-2,2-difluoroethane (HCFC-142)

The conversion of the chloro compound into a fluoro compound may be a direct conversion (with only one reaction step or with only one set of reaction conditions) or an indirect conversion (with two or more than two reaction steps or using two or more than two sets of reaction conditions).

The fluorination reaction may be performed:
with an HF/chloro compound mole ratio of from 3:1 to 150:1, preferably from 4:1 to 100:1 and more particularly preferably from 5:1 to 50:1;
with a contact time of from 1 to 100 s, preferably from 1 to 50 s and more particularly 2 to 40 s (volume of catalyst divided by the total entering stream, adjusted to the operating temperature and pressure);
at an absolute pressure ranging from 0.1 to 50 bar, preferably from 0.3 to 15 bar;
at a temperature (temperature of the catalytic bed) of from 100 to 500° C., preferably from 200 to 450° C. and more particularly from 300 to 400° C.

In order to avoid rapid deactivation of the catalyst during the reaction, an oxidizing agent (for example oxygen or chlorine) may be added, for example in an oxidizing agent/organic compounds mole ratio of from 0.005 to 2, preferably from 0.01 to 1.5. Use may be made, for example, of a stream of pure oxygen or of pure chlorine, or an oxygen/nitrogen or chlorine/nitrogen mixture.

The catalyst used may be based, for example, on a metal comprising an oxide of a transition metal or a derivative or a halide or an oxyhalide of such a metal. Examples that may be mentioned include $FeCl_3$, chromium oxyfluoride, chromium oxides (optionally subjected to fluorination treatments), chromium fluorides, and mixtures thereof. Other possible catalysts are catalysts supported on charcoal, antimony-based catalysts and aluminum-based catalysts (for example $AlF_3$ and $Al_2O_3$, alumina oxyfluoride and alumina fluoride).

Use may generally be made of a chromium oxyfluoride, an aluminum fluoride or oxyfluoride, or an optionally supported catalyst containing a metal such as Cr, Ni, Fe, Zn, Ti, V, Zr, Mo, Ge, Sn, Pb, Mg or Sb.

Reference may be made in this respect to WO 2007/079 431 (on page 7, lines 1-5 and 28-32), to EP 939 071

(paragraph [0022]), to WO 2008/054 781 (on page 9, line 22 to page 10, line 34) and to WO 2008/040 969 (claim 1), to which reference is expressly made.

Before its use, the catalyst is preferably subjected to activation with air, oxygen or chlorine and/or with HF.

Before its use, the catalyst is preferably subjected to activation with air or oxygen and HF at a temperature of from 100 to 500° C., preferably from 250 to 500° C. and more particularly from 300 to 400° C. The activation time is preferably from 1 to 200 hours and more particularly from 1 to 50 hours.

This activation may be followed by a final fluorination activation step in the presence of an oxidizing agent, HF and organic compounds.

The HF/organic compounds mole ratio is preferably from 2 to 40 and the oxidizing agent/organic compounds mole ratio is preferably from 0.04 to 25. The final activation temperature is preferably from 300 to 400° C. and its duration is preferably from 6 to 100 hours.

The catalyst is preferably based on chromium and it is more particularly a mixed catalyst comprising chromium.

According to one embodiment, a mixed catalyst comprising chromium and nickel is used. The Cr/Ni mole ratio (on the basis of the metal element) is generally from 0.5 to 5, for example from 0.7 to 2, for example about 1. The catalyst may contain from 0.5% to 20% by weight of chromium, and from 0.5% to 20% by weight of nickel, preferably from 2% to 10% of each.

The metal may be present in metallic form or in the form of a derivative, for example an oxide, halide or oxyhalide. These derivatives are preferably obtained by activation of the catalytic metal.

The support is preferably constituted with aluminum, for example alumina, activated alumina or aluminum derivatives, such as aluminum halides and aluminum oxyhalides, described, for example, in U.S. Pat. No. 4,902,838, or obtained via the activation process described above.

The catalyst may comprise chromium and nickel in an optionally activated form, on a support that has optionally been subjected to activation.

Reference may be made to WO 2009/118 628 (especially on page 4, line 30 to page 7, line 16), to which reference is expressly made herein.

Another preferred embodiment is based on a mixed catalyst containing chromium and at least one element chosen from Mg and Zn. The atomic ratio of Mg or Zn/Cr is preferably from 0.01 to 5.

With reference to FIG. 1, an embodiment of the invention is now described in the particular case of a process for producing HFO-1234yf from HCC-240db, it being understood that it is similarly valid for other couples of chloro compounds/fluoro compounds.

The installation according to the invention comprises a pipe for supplying the liquid stream of HCC-240db 2 and a pipe for supplying the gas stream comprising HF 5, which feed a catalytic fluorination reactor 8. The pipe for supplying the liquid stream of HCC-240db 2 originates from a reserve of liquid HCC-240db 1. The pipe for supplying the gas stream comprising HF 5 may transport a stream of pure HF (optionally in combination with an oxidizing agent as described above) or, alternately, a mixture of HF and of organic compounds, especially of chloro and/or fluoro organic compounds, as is the case in the illustrated example, and as will be described in greater detail below.

A mixing and vaporizing unit 4 is fed both by the pipe for supplying the liquid stream of HCC-240db 2 and the pipe for supplying the gas stream comprising HF 5. This unit is adapted to mix the gas stream and the liquid stream. It is preferably a static mixer so as to allow a process of continuous type. In this unit, the gas stream comprising HF yields heat to the liquid stream of HCC-240db, which allows vaporization of the HCC-240db.

The mixture of HCC-240db, of HF and optionally of additional compounds is collected in a gas mixture collection pipe 6 at the outlet of the mixing and vaporizing unit 4, which transports the mixture to the catalytic fluorination reactor 8.

The HCC-240db may undergo a preliminary heating step before mixing with the gas stream comprising HF. In this case, this preliminary heating is performed at a temperature below the vaporization temperature of HCC-240db (and at a temperature below the degradation or decomposition temperature of this compound). To this end, heating means 3 may be provided on the pipe for supplying the liquid stream of HCC-240db 2.

Between the mixing of HCC-240db with the stream comprising HF and the fluorination reaction, additional heating of the mixture or, on the contrary, cooling of the mixture may be provided, depending on the case, by providing either heating means or, as illustrated in the figure, cooling means 7 on the gas mixture collection pipe 6. The choice of heating or cooling depends on the desired temperature for the fluorination reaction, in comparison with the temperature of the gas mixture obtained from the mixing and vaporizing unit 4.

A product stream collection pipe 9 is connected at the outlet of the catalytic fluorination reactor 8. This collection pipe feeds a separating unit 10 (or several successive separating units) making it possible especially to separate the product of interest (fluoro compound, in this instance HFO-1234yf) from the rest of the product stream. In this regard, use may be made especially of one or more distillation columns, or decantation, extraction or washing units or the like. This product of interest is recovered in a fluoro compound collection pipe 11 at the outlet of the separating unit 10. Moreover, a recycling stream is recovered in a recycling stream collection pipe 12. Other undesirable products may moreover be removed at this stage (especially the hydrochloric acid generated during the fluorination reaction).

The recycling stream may especially contain unreacted reagents, namely HF and chloro compound (in this instance HCC-240db). It may also contain side products derived from the reaction, i.e. fluoro products obtained by fluorination of the chloro compound (HCC-240db) and other than the desired fluoro compound. In the illustrated case, the recycling stream especially contains HCFO-1233xf, and optionally HFC-245cb (1,1,1,2,2-pentafluoropropane), obtained by fluorination of HCC-240db. According to a possible embodiment, the recycling stream may be returned directly into the catalytic fluorination reactor 8. According to another possible embodiment, it may undergo a completely separate treatment, or even separate upgrading. According to another possible embodiment, it is partially returned to the catalytic fluorination reactor 8.

According to another embodiment, which is the one illustrated here, the recycling stream undergoes an additional fluorination before being returned to the main catalytic fluorination reactor 8.

Thus, the recycling stream collection pipe 12 feeds an additional catalytic fluorination reactor 16. An HF supply pipe 13 may, where appropriate, as illustrated, be connected thereto so as to supply fresh HF.

An oxidizing agent supply pipe 14 may also, where appropriate, as illustrated, be connected to the recycling stream collection pipe 12 so as to provide a supply of oxidizing agent capable of maintaining the catalytic activity of the catalyst.

Heating and vaporizing means 15 may be provided on the recycling stream collection pipe 12 so as to bring the stream to the desired temperature for the additional fluorination reaction, which is performed in the additional catalytic fluorination reactor 16.

In the illustrated example, the pipe for supplying the gas stream comprising HF 5 (described previously) is derived directly from the additional catalytic fluorination reactor 16. Thus, the gas stream comprising HF contains, besides HF (and, where appropriate, oxidizing agent), fluoro products derived from the additional fluorination reaction.

A supply of fresh HF and/or a supply of oxidizing agent may be added into the pipe for supplying the gas stream comprising HF 5, if need be.

The principle of a production process comprising two distinct catalytic fluorination steps, the feeding with chloro reagent (HCC-240db) being performed between these two steps, is described in detail in WO 2013/088 195, to which it is referred by way of reference.

In the preceding description, the gas stream comprising HF (which is used to vaporize the liquid stream of chloro compound) corresponds to a stream derived from an additional fluorination reaction of a recycling stream. Other variants are possible:

- the gas stream comprising HF may be a stream derived from an additional fluorination reaction of a recycling stream, supplemented with additional HF and/or additional oxidizing agent;
- the gas stream comprising HF may be directly a recycling stream or a partial recycling stream (without the additional fluorination reaction step);
- the gas stream comprising HF may be directly a recycling stream (without the additional fluorination reaction step), supplemented with additional HF and/or additional oxidizing agent;
- the gas stream comprising HF may be a stream of fresh HF optionally comprising fresh oxidizing agent.

In the latter case, if a recycling stream is present, it may be introduced after the step of mixing the gas stream comprising HF with the liquid stream of chloro compound; and if an additional fluorination reaction of a recycling stream is performed, the stream derived from this reaction may be introduced after the step of mixing the gas stream comprising HF with the liquid stream of chloro compound.

Figure 2:
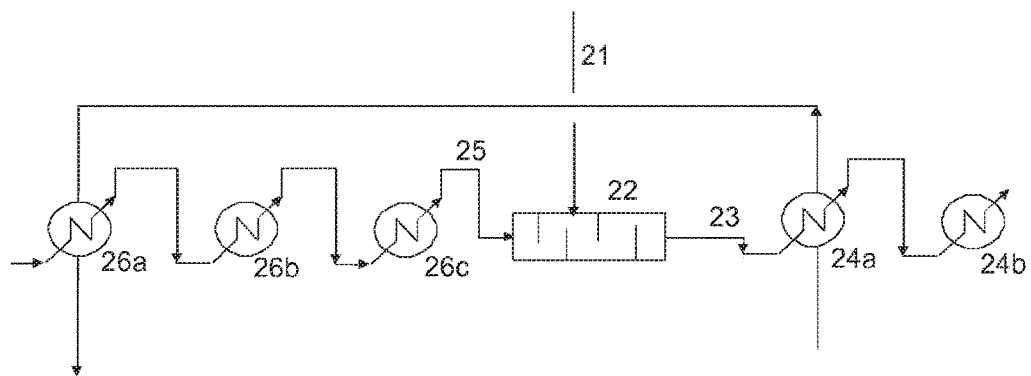
FIG. 2 schematically represents another embodiment of the installation according to the invention.

Another embodiment is now described with reference to FIG. 2: it is a process for producing HFC-125 from PER (and also the installation for implementing said process).

The installation comprises a pipe for supplying the gas stream comprising HF 25 and a pipe for supplying the liquid stream of PER 21, which both feed a mixing and vaporizing unit 22, which is a static mixer. A gas mixture collection pipe 23 is connected at the outlet of said unit, and feeds one or a series of several fluorination reactors (not shown).

Heating means 26a, 26b, 26c are provided on the pipe for supplying the gas stream comprising HF 25. Heating means 24a, 24b are provided on the gas mixture collection pipe 23.

According to one embodiment, the gas stream comprising HF is obtained by heating and, where appropriate, vaporizing a recycling stream collected after treatment and separation of a product stream derived from the catalytic fluorination reaction.

Some of the heating means 26a, 24a used may be heat-saving exchangers.

The important parameters to be taken into account generally in the implementation of the process of the invention are the following:

- the flow rate of gas stream comprising HF must be higher than the flow rate of chloro compound, and sufficiently high relative to the latter so as to allow total vaporization of the chloro compound and to avoid partial condensation of the gas stream comprising HF; thus, preferably, the ratio of mass flows between the gas stream comprising HF and the stream of chloro compound is from 1 to 30, preferably from 1.2 to 25 and more particularly preferably from 1.5 to 20;
- the temperature of the gas stream comprising HF must be sufficiently high, for the same reasons (it must in any event be higher than the vaporization temperature of the chloro compound, at the pressure under consideration);
- the differential between the temperature of the gas stream comprising HF and the temperature of the gas mixture after vaporization of the chloro compound must remain relatively low, preferably less than or equal to 50° C., or less than or equal to 30° C. or 25° C.

When the temperature of the gas stream comprising HF is relatively low (for example of the order of 150 or 200° C.), a relatively high mass flow rate (gas stream/liquid stream) ratio is necessary so as to ensure total vaporization of the chloro compound. However, the resulting temperature differential is relatively low. In this regime, the heat generated by oligomerization of the HF is used to vaporize the chloro compound.

When the temperature of the gas stream comprising HF is relatively high (for example of the order of 250 or 300° C.), a lower mass flow rate ratio is necessary, but the temperature differential obtained is relatively high. In this regime, the HF vapor is not in oligomeric form, and the heat of vaporization of the chloro compound is provided by the cooling of the superheated HF.

EXAMPLES

The examples that follow illustrate the invention without limiting it.

Example 1

Study of the Lowering of the Temperature of the HF Stream Associated with Mixing with the Chloro Compound For this study, a fluorination reaction of HCC-240db to HFO-1234yf is considered, according to the scheme of FIG. 1.

A productivity of HFO-1234yf of 1600 kg/h, a fluorination reaction (reactor 8) performed at 4, 5 or 7 bar absolute, depending on the case, an HF/chloro compound mole ratio of 10, 20 or 30, depending on the case, and a degree of conversion of HCFO-1233xf of 60% or 70%, depending on the case, are considered. The feed rate of HCC-240db is 3100 kg/h in all cases.

The preliminary fluorination reaction (reactor 16) is considered to be performed at a temperature of 350° C., and the gas stream comprising HF (pipe 5) is thus considered to be at this temperature of 350° C.

Three conditions concerning the temperature of the stream of HCC-240db are considered: 25° C. (absence of preheating of the stream), 70° C. or 100° C.

Figure 3:
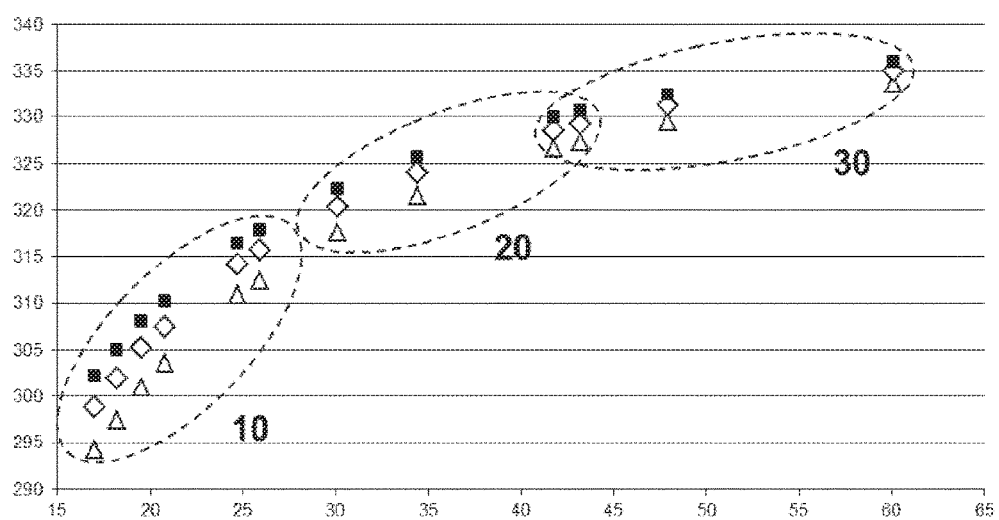
FIG. 3 is a graph illustrating the change in temperature of a feed stream of the main fluorination reactor after vaporization of the chloro compound (cf. Example 1). The x-axis gives the flow rate of the gas stream comprising HF, expressed in t/h; the y-axis gives the temperature of the stream after mixing with the chloro compound and vaporization thereof, expressed in ° C. The points represented by Δ correspond to an initial temperature of the chloro compound of 25° C., those represented by ■ correspond to an initial temperature of the chloro compound of 70° C. and those represented by ◊ correspond to an initial temperature of the chloro compound of 100° C. The three groups of data marked 10, 20 and 30 on the graph correspond to HF/organics mole ratios respectively equal to 10, 20 and 30.

Starting with all of these conditions, the temperature of the stream after mixing between the stream comprising HF and the liquid stream of HCC-240db is calculated in each case, from the available data regarding the vapor pressure as a function of the temperature for HCC-240db. The results are given in FIG. 3.

It is found that the influence of preheating of the stream of HCC-240db on the final temperature is relatively small (difference of 2.4 at 8° C. on the final temperature of the stream after mixing, depending on whether the stream of HCC-240db is or is not preheated). The need to provide additional heating (or, on the contrary, cooling) of the mixture before the reaction depends on the desired reaction temperature.

It is found, in general, that the decrease in temperature associated with the mixing with HCC-240db and vaporization thereof is moderate and compatible with the implementation of the process.

Example 2

Study of the Mass Flow Rate Ratio Required Between the Gas Stream Comprising Hf and the Stream of Chloro Compound For this study, the same basic conditions as in Example 1 are used, taking a pressure of 7 bar absolute. Streams of HF (pure) at various temperatures, namely 150, 200, 250 or 300° C., are envisaged here. Depending on the case, a greater or lesser decrease in temperature following mixing with HCC-240db (noted ΔT, as an absolute value) is accepted, and the corresponding mass flow rate ratio (R) (mass flow rate of gas stream comprising HF to mass flow rate of HCC-240db) is deduced therefrom.

The limit values of ΔT and R allowing total vaporization of the HCC-240db (without leading to condensation of the gas stream comprising HF) are also calculated. The results are collated in the table below:

|  | ΔT = 50° C. | ΔT = 30° C. | ΔT = 25° C. | Limit for total vaporization |
|---|---|---|---|---|
| HF stream at 150° C. | Impossible | Impossible | R = 2.9 | R = 2.6 (i.e. ΔT = 26° C.) |
| HF stream at 200° C. | R = 2.9 | R = 5.6 | R = 6.9 | R = 1.8 (i.e. ΔT = 66° C.) |
| HF stream at 250° C. | R = 4.3 | R = 7.6 | R = 9.4 | R = 1.3 (i.e. ΔT = 109° C.) |
| HF stream at 300° C. | R = 5.1 | R = 9.0 | R = 10.9 | R = 1.1 (i.e. ΔT = 152° C.) |

Example 3

Pilot Test

A gas stream derived from a fluorination reactor comprising HF is mixed with a preheated liquid stream of 240db. The flow rate of the gas stream comprising HF derived from the fluorination reactor is from 20 to 50 kg/h. This gas stream is at a temperature of from 320° C. to 350° C. and at a pressure of 3 to 5 bara. The flow rate of the liquid stream of 240db is from 3 to 4 kg/h. This liquid stream of 240db is preheated to a temperature of 100° C. to 120° C. at a pressure of 4 to 6 bara.

When the two streams are mixed, the liquid stream of 240db is instantaneously vaporized by the stream comprising HF and the temperature of the gas stream resulting from the mixing of these two streams is from 280° C. to 330° C. at 3 to 5 bara. This resulting stream may optionally be reheated to a temperature of 350° C. to 380° C. before feeding another fluorination reactor in which the fluorination of 240db to 1233xf is performed.

The invention claimed is:

1. An installation for producing a fluoro compound, comprising:
    a pipe for supplying a liquid stream of chloro compound;
    a pipe for supplying a gas stream comprising hydrofluoric acid;
    a mixing and vaporizing unit fed by the pipe for supplying the liquid stream of chloro compound and the pipe for supplying the gas stream comprising hydrofluoric acid;
    a pipe for collecting a gas mixture at the outlet of the mixing and vaporizing unit;
    a catalytic fluorination reactor fed by the pipe for collecting the gas mixture, wherein the installation comprises a mixing and vaporizing unit interposed between the pipe for supplying the liquid stream of chloro compound and the pipe for supplying the gas stream comprising hydrofluoric acid and the catalytic fluorination reactor; and
    a pipe for collecting the product stream at the outlet of the catalytic fluorination reactor.

2. The installation as claimed in claim 1, wherein:
    the chloro compound comprises a chlorocarbon, a chlorohydrocarbon, a chlorofluorocarbon, a hydrochlorofluorocarbon, a chloroolefin, a hydrochloroolefin or a hydrochlorofluoroolefin; and wherein the fluoro compound comprises a fluorocarbon, a fluorohydrocarbon, a chlorofluorocarbon, a hydrochlorofluorocarbon, a fluoroolefin, a hydrofluoroolefin or a hydrochlorofluoroolefin.

3. The installation as claimed in claim 1, wherein the mixing and vaporizing unit) is a static mixer.

4. The installation as claimed in claim 1, comprising:
    at least one separating unit fed by the product stream collection pipe; and
    a fluoro compound collection pipe and a recycling stream collection pipe at the outlet of the separating unit(s).

5. The installation as claimed in claim 4, wherein the recycling stream collection pipe and optionally a hydrofluoric acid supply pipe feed the pipe for supplying the gas stream comprising hydrofluoric acid.

6. The installation as claimed in claim 4, comprising a catalytic fluorination reactor at least partly fed by the recycling stream collection pipe with a supply of hydrofluoric acid, the pipe for supplying the gas stream comprising hydrofluoric acid being derived from the catalytic fluorination reactor.

7. The installation as claimed in claim 1, comprising heating means on the pipe for supplying the liquid stream of chloro compound.

8. The installation as claimed in claim 1, comprising heating means or cooling means on the gas mixture collection pipe.

* * * * *